United States Patent
Zacharopoulos et al.

(10) Patent No.: US 9,254,217 B2
(45) Date of Patent: Feb. 9, 2016

(54) DEVICE FOR RESTRAINT OF PATIENTS ON A TABLE

(71) Applicant: AKTINA CORP., Congers, NY (US)

(72) Inventors: Nicholas G. Zacharopoulos, Congers, NY (US); Milan Markovic, Congers, NY (US)

(73) Assignee: AKTINA CORP., Congers, NY (US)

(*) Notice: Subject to any disclaimer, the term of this patent is extended or adjusted under 35 U.S.C. 154(b) by 183 days.

(21) Appl. No.: 14/055,433

(22) Filed: Oct. 16, 2013

(65) Prior Publication Data

US 2014/0107393 A1 Apr. 17, 2014

Related U.S. Application Data

(60) Provisional application No. 61/714,535, filed on Oct. 16, 2012.

(51) Int. Cl.
| | | |
|---|---|---|
| *A61F 5/37* | (2006.01) | |
| *A61G 13/10* | (2006.01) | |
| *A61G 13/12* | (2006.01) | |
| *A61N 5/10* | (2006.01) | |

(52) U.S. Cl.
CPC ................ *A61F 5/3776* (2013.01); *A61N 5/10* (2013.01); *A61G 13/101* (2013.01); *A61G 13/1275* (2013.01); *A61N 2005/1097* (2013.01)

(58) Field of Classification Search
CPC ..... A61G 13/10; A61G 13/101; A61G 13/12; A61G 13/1205; A61G 13/121; A61G 13/122; A61G 13/1225; A61G 13/123; A61G 13/1235; A61G 13/124; A61G 13/1245; A61G 13/125; A61G 13/1255; A61G 13/126; A61G 13/1275; A61F 5/37; A61F 5/3707; A61F 5/3761; A61F 5/3769; A61F 5/3776
USPC ............ 5/621–624, 637, 646–648, 650, 658; 128/845, 846, 869, 870, 876–882
See application file for complete search history.

(56) References Cited

U.S. PATENT DOCUMENTS

| | | | | |
|---|---|---|---|---|
| 1,632,160 | A * | 6/1927 | Barnes .............................. | 27/13 |
| 2,199,949 | A * | 5/1940 | Davis .............................. | 27/21.1 |
| 2,535,559 | A * | 12/1950 | Wolf ................................ | 5/630 |
| 3,302,021 | A * | 1/1967 | Hardy ........................... | 378/174 |
| 3,823,709 | A * | 7/1974 | McGuire ....................... | 600/230 |
| 3,844,550 | A * | 10/1974 | McGuire .......................... | 5/621 |
| 4,045,678 | A * | 8/1977 | Rickard ......................... | 378/174 |
| 4,181,297 | A * | 1/1980 | Nichols ............................ | 5/650 |
| 4,299,213 | A * | 11/1981 | Violet ........................... | 128/882 |
| 4,526,355 | A * | 7/1985 | Moore et al. ..................... | 5/624 |
| 4,583,725 | A * | 4/1986 | Arnold ............................ | 5/621 |
| 4,771,493 | A * | 9/1988 | Park ................................ | 5/637 |
| 4,903,689 | A * | 2/1990 | Lannertone ................... | 606/243 |
| 4,913,413 | A * | 4/1990 | Raab ................................ | 5/624 |

(Continued)

*Primary Examiner* — Robert G Santos
(74) *Attorney, Agent, or Firm* — Donald J. Ranft; Kristen A. Mogavero; Collen IP (57) ABSTRACT

The present invention is a device for the restraint of patients on a treatment table. More specifically, the invention is designed to provide lateral side pressure on a patient in the abdomen, thorax, and hip areas during a radiation treatment. The main components of the device are paddle(s) and at least one crossbar assembly. The paddles are coupled to a crossbar assembly, which is positioned on a treatment table under the body cushion in which the patient is positioned. The paddles can be moved laterally along the crossbar such that they put lateral pressure on the cushion and the patient.

9 Claims, 8 Drawing Sheets

(56) References Cited

U.S. PATENT DOCUMENTS

| | | | |
|---|---|---|---|
| 5,832,550 A * | 11/1998 | Hauger et al. | 5/621 |
| 5,944,677 A * | 8/1999 | Richard | 602/23 |
| 6,003,176 A * | 12/1999 | Wasley et al. | 5/624 |
| 6,076,525 A * | 6/2000 | Hoffman | 128/845 |
| 6,154,901 A * | 12/2000 | Carr | 5/621 |
| 6,311,349 B1 * | 11/2001 | Kazakia et al. | 5/624 |
| 6,637,057 B2 * | 10/2003 | Phillips et al. | 5/637 |
| 6,941,951 B2 * | 9/2005 | Hubert et al. | 128/845 |
| 7,120,954 B2 * | 10/2006 | Traut et al. | 5/637 |
| 7,426,930 B1 * | 9/2008 | Bailey et al. | 128/845 |
| 7,600,281 B2 * | 10/2009 | Skripps | 5/621 |
| 7,753,863 B2 * | 7/2010 | Richard | 602/23 |
| 8,234,730 B2 * | 8/2012 | Skripps | 5/621 |
| 2002/0073487 A1 * | 6/2002 | Phillips et al. | 5/628 |
| 2004/0016057 A1 * | 1/2004 | Traut et al. | 5/628 |
| 2004/0049852 A1 * | 3/2004 | Phillips et al. | 5/626 |
| 2005/0081865 A1 * | 4/2005 | Hubert et al. | 128/845 |
| 2006/0248650 A1 * | 11/2006 | Skripps | 5/621 |
| 2007/0000500 A1 * | 1/2007 | Richard | 128/869 |
| 2010/0024128 A1 * | 2/2010 | Skripps | 5/621 |
| 2014/0107393 A1 * | 4/2014 | Zacharopoulos et al. | 600/1 |
| 2014/0261448 A1 * | 9/2014 | Knight | A61H 37/00 128/845 |

* cited by examiner

DEVICE FOR RESTRAINT OF PATIENTS ON A TABLE

FIELD OF THE INVENTION

The invention disclosed herein is related to the field of medical devices, specifically devices for the positioning and restraint of patients on a table.

BACKGROUND

Radiotherapy requires that the patient remain very still and not move for the duration of the treatment. Known techniques for restraining the patient either place the patient onto a cushion or into a structure that contains a cushion (a "cradle"). One of the main problems with these two approaches is that the patient can move laterally. The main advantage of the disclosed invention is that the system applies lateral force on the patient to reduce movement during treatment. Furthermore, the paddles used to apply the lateral pressure may be placed in customized locations and positions for each patient.

Another problem with known cradle apparatuses for restraining patients is that they generally require a base plate to be placed onto the treatment couch to accommodate all the cradle accessories. Since radiation therapy requires that treatment beams enter the patient from multiple entry angles, the extra material below the patient attenuates the beam in unpredictable ways. An additional advantage of the disclosed invention is that the system does not require a base plate.

SUMMARY

The invention provides lateral side pressure on the patient during treatment to restrain them and stabilize their position. More specifically, the invention is designed to provide lateral side pressure on the patient in the abdomen, thorax, and hip areas during a radiation treatment. This is achieved through the use of lateral side paddles, attached to a crossbar assembly, whereby the position of the paddles can be adjusted and customized for each patient.

PARTS LIST

1. Paddle
2. Crossbar Assembly
3. End Bracket
4. Strap
5. Slider
6. Attachment Pin
7. Support Rod
8. Bridge
9. Buckle Lever
10. Paddle Lock
11. Bridge Pin
12. Slider Pin
13. Slider Roller
14. Buckle Pin
15. Attachment Hole
16. Patient Cushion
17. Treatment Couch
18. Locking Key
19. Slider Roller
20. Paddle Lock Plate

DETAILED DESCRIPTION

Figure 1:
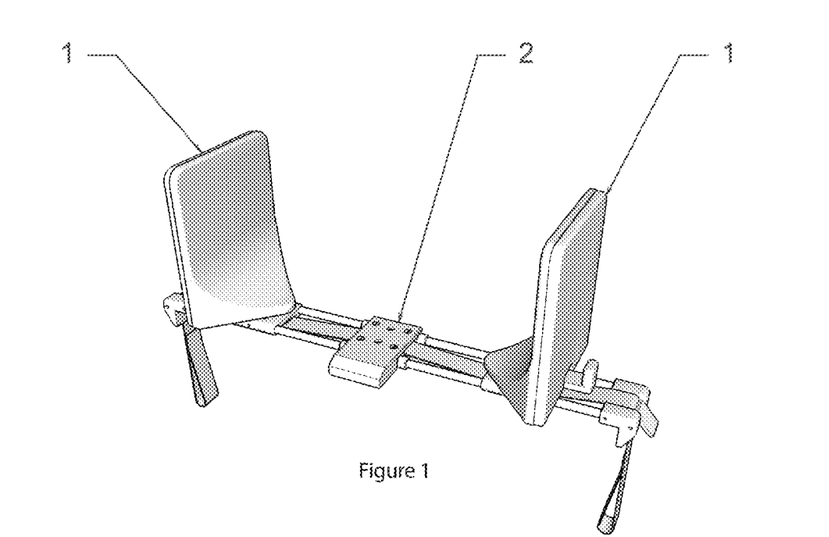
FIG. 1 is a perspective view of the paddles and crossbar assembly.

FIG. 1 one shows the main components of the system—the paddle 1 and crossbar assembly 2. Each crossbar assembly is intended to be used with 2 paddles. The paddles are capable of being moved laterally along the crossbar assembly and are easily attached and detached from the crossbar assembly. The paddles depicted are shaped such that they slope outwards at the base in order to better contour the patient's body.

Figure 2:
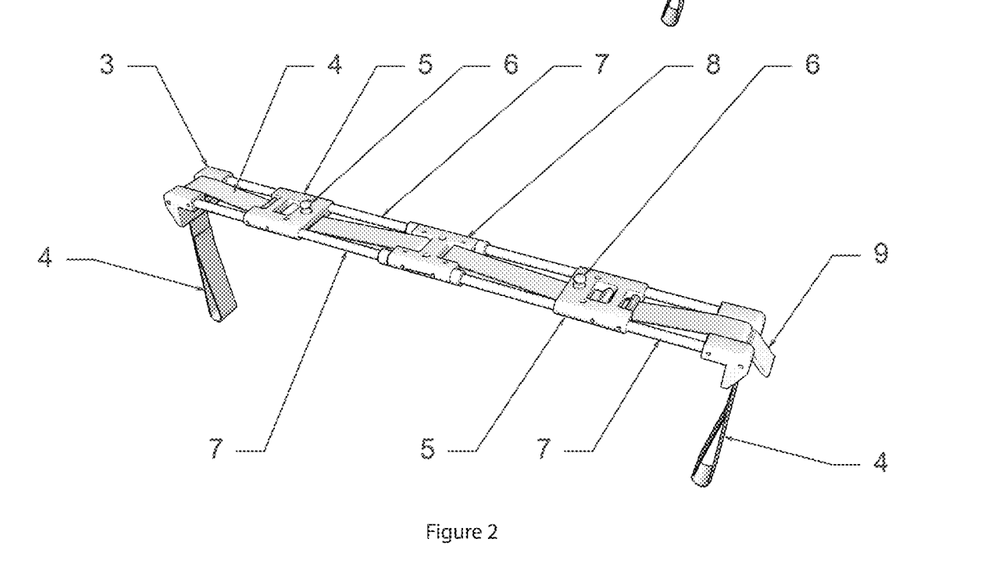
FIG. 2 is a perspective view of the crossbar assembly.

FIG. 2 shows a detailed view of the crossbar assembly. The paddles 1 are attached to the sliders 5. The crossbar assembly is positioned on the treatment couch 17 (FIG. 9) and is stabilized by the two end brackets 3.

Figure 4:
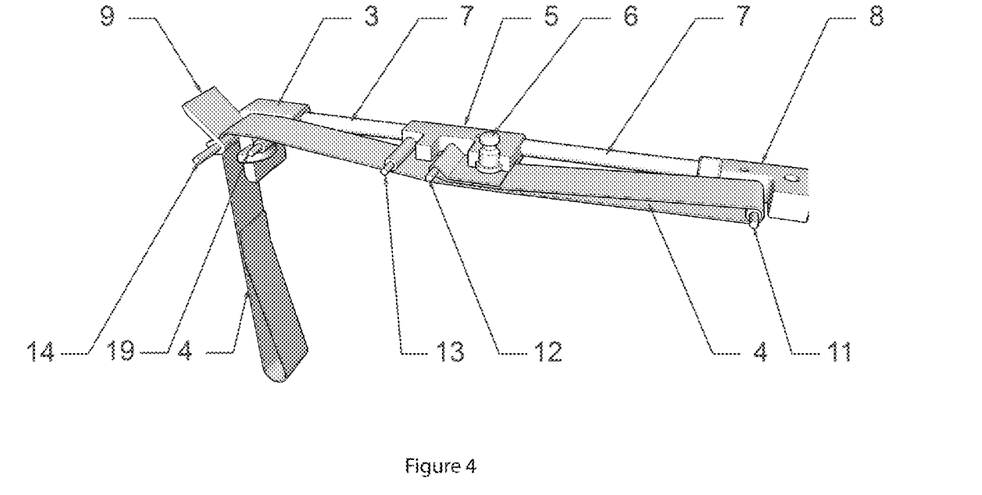
FIG. 4 is a partial cross-sectional view of the crossbar assembly from one end bracket to the bridge.
Figure 5:
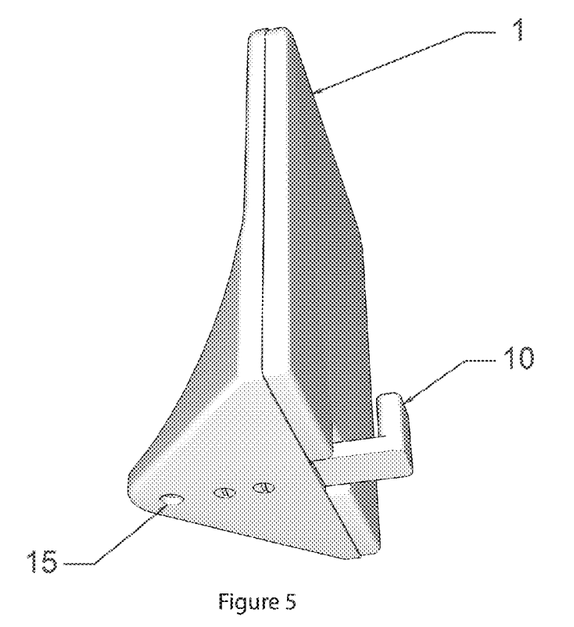
FIG. 5 is a bottom perspective view of a paddle.
Figure 6:
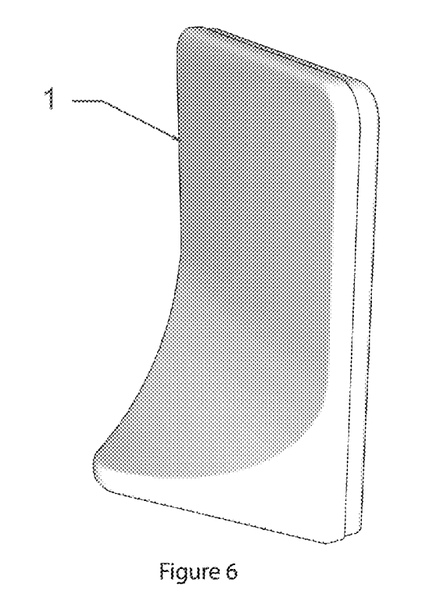
FIG. 6 is a front perspective view of a paddle.
Figure 7:
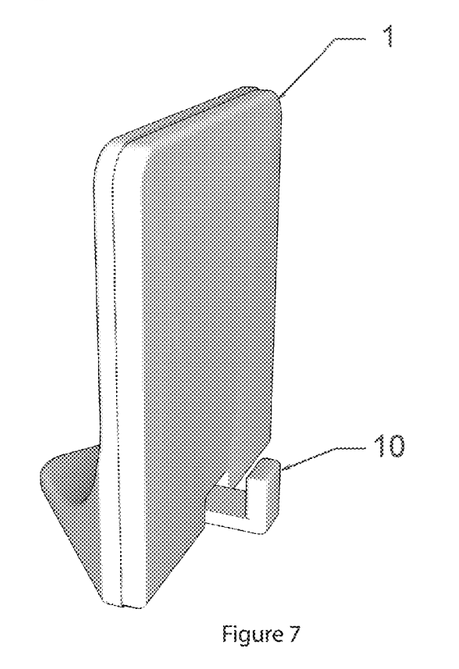
FIG. 7 is a side perspective view of a paddle.

The paddle 1 can be seen in FIG. 5 (bottom), FIG. 6 (front) and FIG. 7 (back). Each paddle 1 has an attachment hole 15 as can be seen in FIG. 5. The attachment hole 15 drops over the attachment pin 6 of the slider 5 (FIG. 4).

Figure 3:
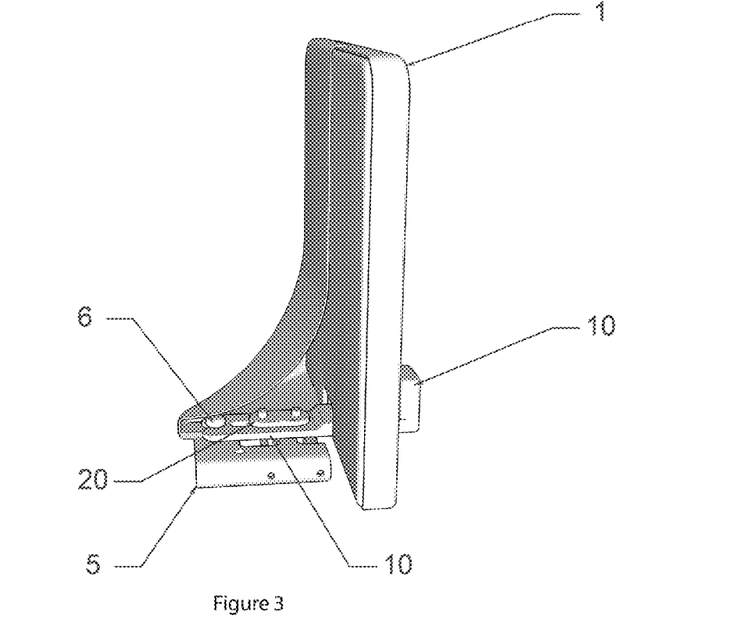
FIG. 3 is a cross-sectional view of a paddle illustrating its connection to the slider.
Figure 16:
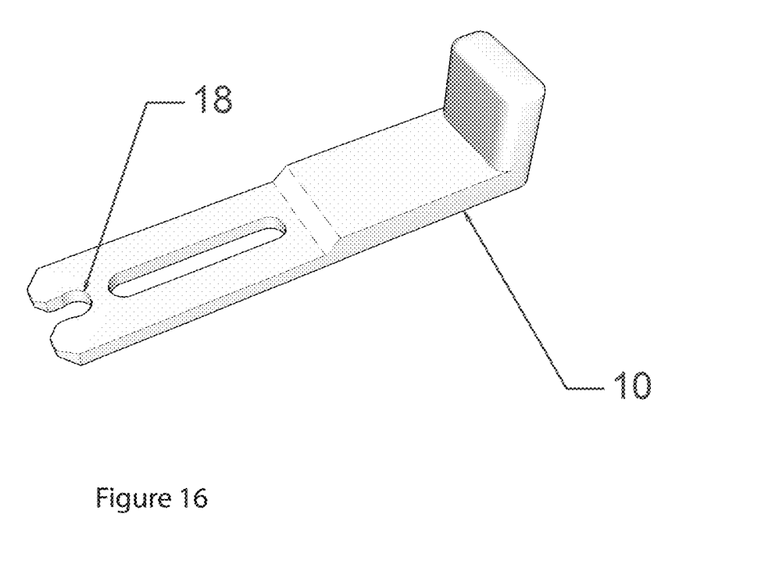
FIG. 16 is a top perspective view of the lock piece.

FIG. 3 shows a cross-section of the paddle 1 when it is interlocked with the slider 5. The paddle contains a lock 10 which is used to lock and release the paddle from the slider 5. FIG. 16 shows a detailed view of the lock 10. The engaging end of the lock 10 has a key 18 which slides under the head of the attachment pin 6. The lock 10 can slide horizontally towards and away from the attachment pin 6. When the lock 10 is moved away from the attachment pin 6, the paddle 1 can be removed from the slider 5. When the lock 10 is engaged (moved towards the attachment pin 6), the key 18 slides under the head of the attachment pin 6, and the paddle 1 is thereby locked into place. Since the paddle 1 is fixed to the slider 5 via only the attachment pin 6, the paddle 1 is able to rotate about the attachment pin 6 when it is in the locked position.

The strap 4 (FIG. 4) is used to apply pressure on the slider 5 and thereby adjust its position, and the position of the paddles 1 when they are attached to the slider 5. By pulling down on the strap 4, the slider 5 will move towards the bridge 8. Details of this mechanism can be seen in FIG. 4. The strap 4 passes through the buckle lever 9 of the end bracket 3, passes over slider roller 19, passes under pin 13, passes under the slider 5, loops around the bridge pin 11 and then terminates at the slider pin 12. The strap may be secured to the slider pin in any number of ways. As shown in FIG. 4, the strap 4 may include a loop at its end that is placed over the slider pin 12. And the number and layout of slider rollers may be varied as warranted.

Figure 8:
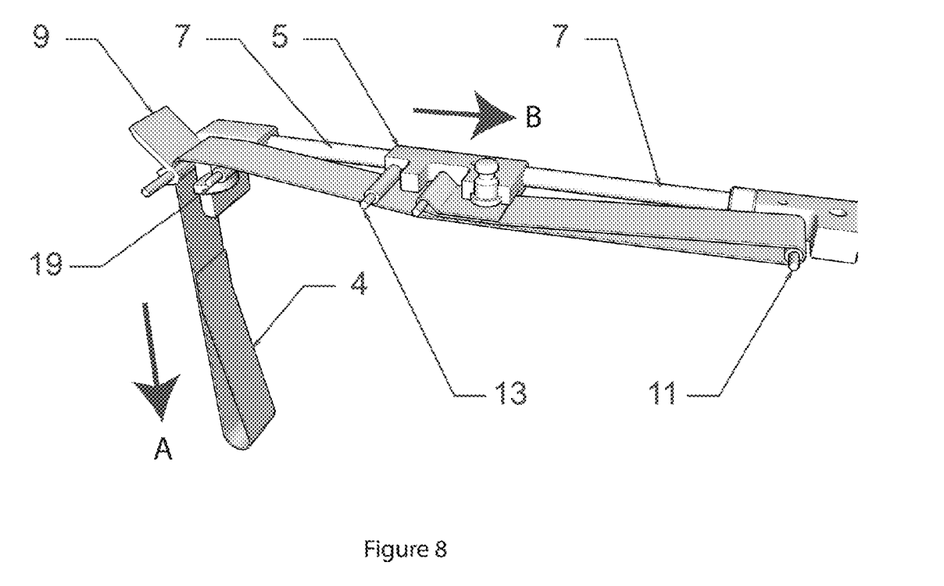
FIG. 8 is a partial cross-sectional view of the crossbar assembly from one end bracket to the bridge illustrating how the strap and buckle lever are used to adjust and secure the position of the slider.

FIG. 8 illustrates the process of adjusting the position of the slider 5. By pulling in the direction "A" on the strap 4, the strap will pull the slider 5 in direction "B." The slider 5 moves laterally along the support rods 7, which pass directly through the slider 5. The bridge 8 is fixed at the center of the crossbar assembly such that it cannot slide along the support rods 7. Once the slider 5 is in the desired position, it may be locked into place by applying the respective buckle lever 9 which rotates on pin 14. By pushing down on the buckle lever 9 which has an offset cam, the strap is wedged between the buckle lever 9 and the end bracket 3. This locks the slider 5 in place since any force exerted by the patient will be outward pressure on the paddle 1 in the direction opposite of direction B, as indicated in FIG. 8.

Figure 9:
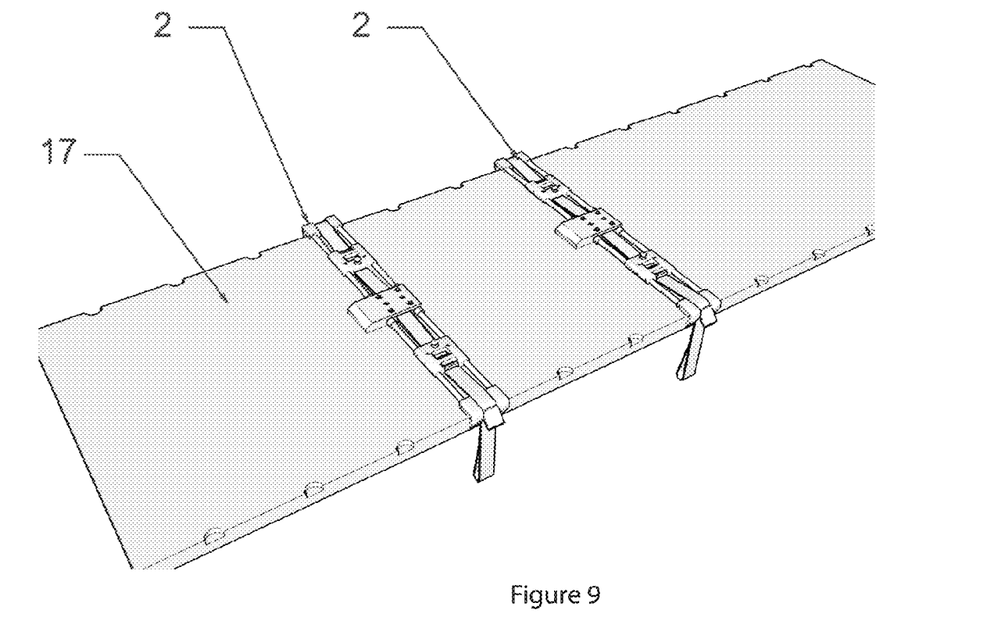
FIG. 9 is a top perspective view of the crossbar assembly positioned on a treatment couch.
Figure 10:
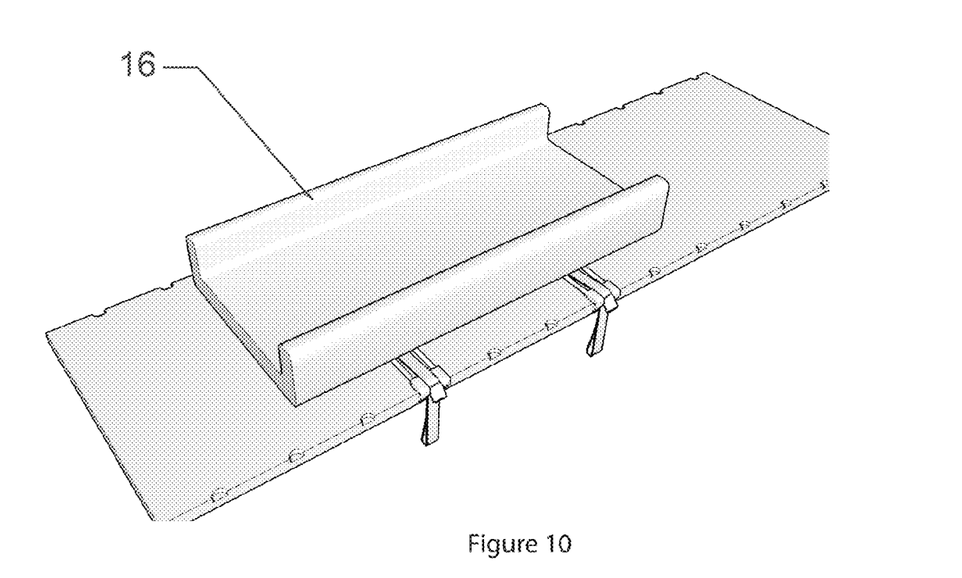
FIG. 10 is a top perspective view of the crossbar assembly and patient cushion positioned on a treatment couch.

FIGS. 9 through 15 illustrate the intended method of use of the disclosed restraint device. As shown in FIG. 9, two crossbar assemblies 2 are positioned in the standard indentations of clinical treatment couches 17. Then a body cushion 16 is placed over the crossbar assemblies (see FIG. 10). This cushion 16 is of the type that can harden after the patient's position is set. Hardening can be accomplished by different techniques, but vacuum bags or two-part epoxy bags are the most common.

Figure 11:
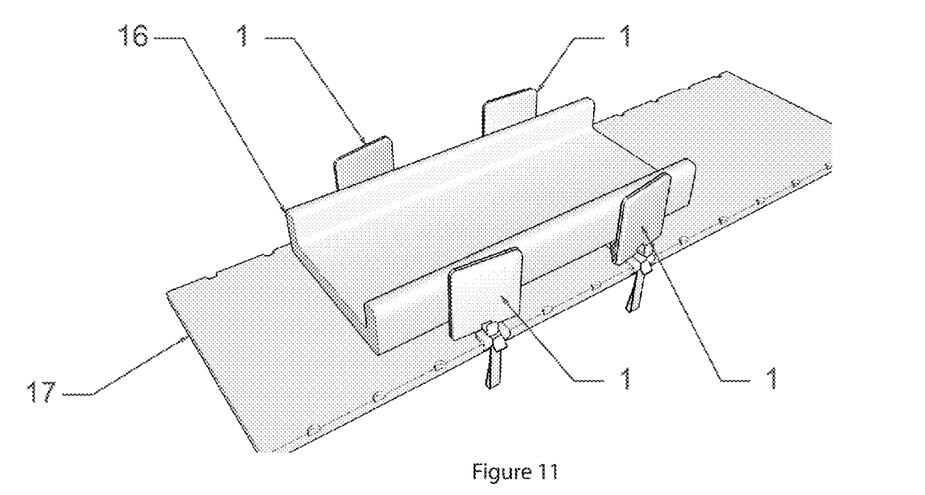
FIG. 11 is a top perspective view of the crossbar assembly, patient cushion, and paddles positioned on a treatment couch.
Figure 12:
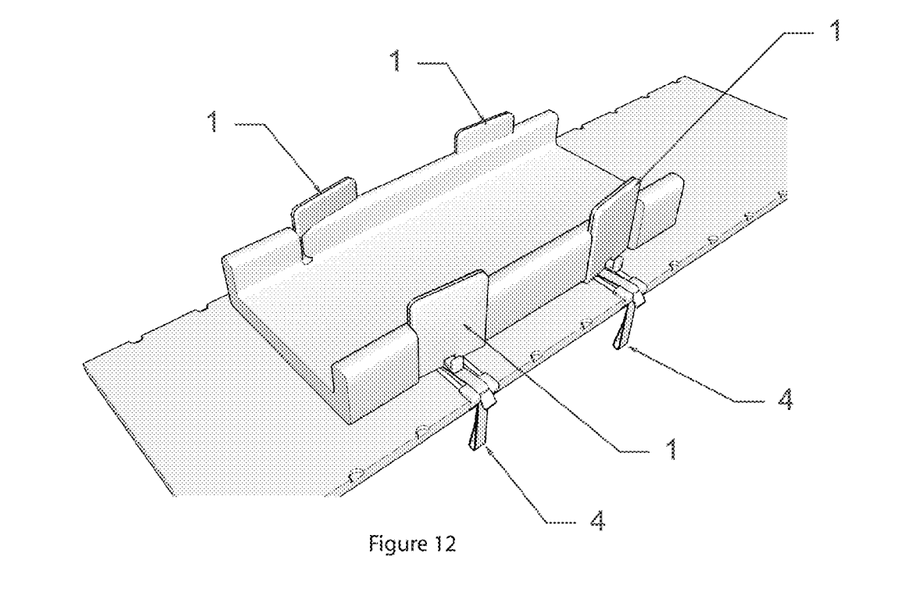
FIG. 12 is a top perspective view of the crossbar assembly, patient cushion, and paddles positioned on a treatment couch where the position of the paddles has been adjusted to fit the patient.

Once the patient is positioned within the body cushion 16, the four paddles 1 are then attached to the sliders 5 of the crossbar assemblies 2 such that the attachment pin 6 of the slider 5 is inserted into the attachment hole 15 of the paddle 1. The lock 10 is moved horizontally towards the attachment pin 6 whereby the key 18 slides under the head of the attachment pin 6, thereby securing the paddle 1 to the slider 5. The paddle 1 is capable of rotating around the attachment pin 6. The strap 4 is then used, as described above, to move the slider 5 and paddle 1 into the desired position against the sides of the body cushion 16. The four paddles 1 and sliders 5 are then locked into place by applying the respective buckle levers 9. The body cushion 16 is then allowed to harden. Once the body cushion is hardened it prevents rotation of the paddles and thus prevents movement of the patient.

Figure 13:
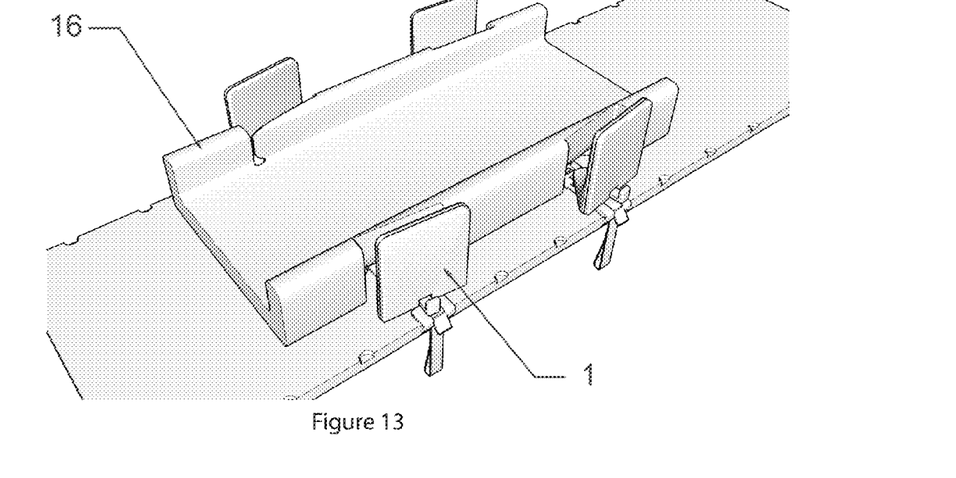
FIG. 13 is a top perspective view of the crossbar assembly, patient cushion, and paddles positioned on a treatment couch where the paddles have been moved away from the patient.
Figure 14:
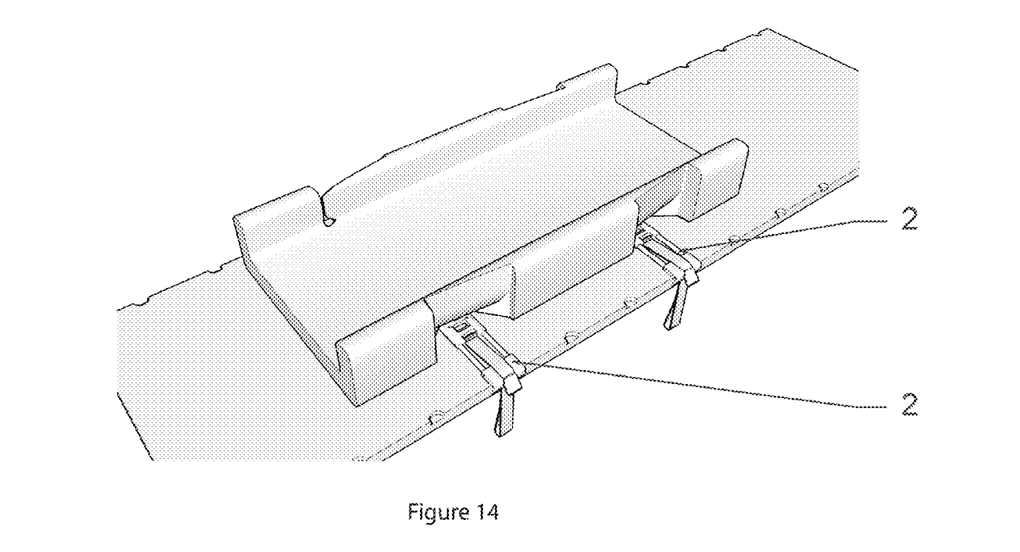
FIG. 14 is a top perspective view of the crossbar assembly and patient cushion with the paddles removed.
Figure 15:
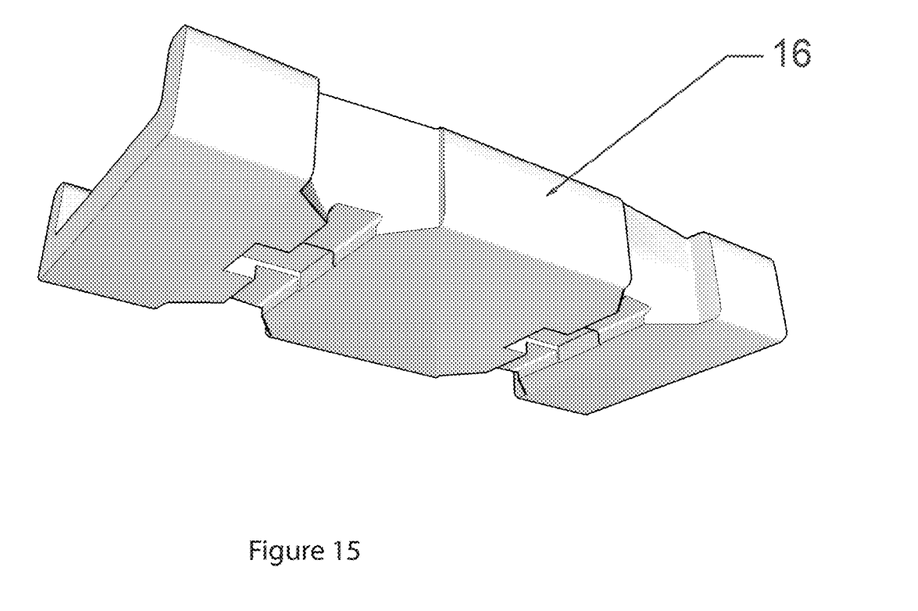
FIG. 15 is a bottom perspective view of the patient cushion after the paddles have been applied and the cushion has been allowed to harden.

As depicted in FIGS. 13 and 14, when the treatment is complete, the patent may be removed from the restraint by first releasing each of the four buckle levers 9 and sliding the sliders 5 and paddles 1 away from the patient. When the paddles 1 are released the body cushion 16 retains the shape and size of the indentation of each paddle 1. This will allow the paddles 1 to be placed in the identical position for the next treatment. The bottom of the body cushion 16 also retains the indentations of the crossbar assemblies 2, so that the exact lateral position of the body cushion 16 will always be fixed relative to treatment couch 17 (see FIG. 15).

The above illustrates various concepts, structures and techniques which are the subject of this patent. It will now become apparent to those of ordinary skill in the art that other embodiments incorporating these concepts, structures and techniques may be used. Accordingly, it is submitted that that scope of the patent should not be limited to the described embodiments but rather should be limited only by the spirit and scope of the following claims. For example in other embodiments different mechanism(s) are used for positioning and securing the paddles in place such as by using an electrical motor drive or hydraulics. The mechanisms (number of rollers, pins, loops, etc) for using straps are configured differently in other embodiments.

The invention claimed is:

1. A device for restraining patients comprising:
a cross bar assembly sized to fit into standard indentations of a treatment couch and is constructed such that a bridge is located in a center of the assembly and secures one end of each of two support rods projecting horizontally from opposite sides of the bridge; an opposite end of each pair of support rods are connected to an end bracket having a buckle lever attached thereto; two support rods on each side of the bridge pass through openings in an associated slider such that the sliders are capable of moving along a length of the support rods between the end brackets and the bridge; on each side of the bridge, a strap passes through the end bracket, passes under at least one roller in the slider closest to the end bracket through which the strap passed, loops around a pin in the bridge and then terminates at and is attached to a pin in the slider under which the strap was passed; and
one or more paddles capable of being coupled to the cross bar assembly in such a way that the one or more paddles are permitted to move laterally along the cross bar assembly and also being temporarily fixed in a set position on the cross bar assembly.

2. A device for restraining patients according to claim 1 further comprising a patient cushion designed to be positioned on a top of the cross bar assembly and wherein the cross bar assembly is designed to be secured to a treatment table.

3. A restraining device according to claim 2 wherein a paddle is capable of being coupled to each slider and the patient cushion is designed to be able to be hardened.

4. A restraining device according to claim 1 wherein a paddle is capable of being coupled to the slider.

5. A restraining device according to claim 4 wherein the paddle includes an attachment hole in its base and a lock piece including a key at one end of the lock piece and is capable of being moved as required for locking and unlocking.

6. A restraining device according to claim 5 wherein the sliders each include an attachment pin which protrudes orthogonally from a top surface of the slider, is sized to be inserted into the attachment hole of the paddle, and is shaped in such a way that the attachment pin has a throat section of a narrower width so that the throat section can be inserted into the key of the lock piece.

7. A restraining device according to claim 4 wherein the one or more paddles are capable of being coupled to the sliders by placing the attachment pin of the slider into the attachment hole of the paddle and sliding the lock piece of the paddle towards the attachment pin such that the key admits the throat section of the attachment pin.

8. A method for restraining a patient on a treatment couch comprising:
creating two paddles;
creating a crossbar assembly sized to fit into standard indentations of a treatment couch and is constructed such that a bridge is located in a center of the assembly and secures one end of each of two support rods projecting horizontally from opposite sides of the bridge; an opposite end of each pair of support rods are connected to an end bracket having a buckle lever attached thereto; two support rods on each side of the bridge pass through openings in an associated slider such that the sliders are capable of moving along a length of the support rods between the end brackets and the bridge; on each side of the bridge, a strap passes through the end bracket, passes under at least one roller in the slider closest to the end bracket through which the strap passed, loops around a pin in the bridge and then terminates at and is attached to a pin in the slider under which the strap was passed;

placing the crossbar assembly in the standard indentations of a treatment couch;

placing a body cushion over the crossbar assembly;

coupling a paddle to each of the two sliders;

moving the coupled paddles and sliders into the desired position manually or by pulling downward on the straps;

securing the paddles and sliders in place by engaging the respective buckle lever; and allowing the body cushion to harden.

9. A method for restraining a patient on a treatment couch comprising:

creating two paddles which each have an attachment hole in base of the paddle thereof and include a lock piece, with a key at one end, capable of being moved horizontally;

creating a crossbar assembly sized to fit into standard indentations of a treatment couch and is constructed such that a bridge is located in a center of the assembly and secures one end of each of two support rods projecting horizontally from opposite sides of the bridge; an opposite end of each pair of support rods are connected to an end bracket having a buckle lever attached thereto; two support rods on each side of the bridge pass through openings in an associated slider such that the sliders are capable of moving along a length of the support rods between the end brackets and the bridge; on each side of the bridge, a strap passes through the end bracket, passes under at least one roller in the slider closest to the end bracket through which the strap passed, loops around a pin in the bridge and then terminates at and is attached to a pin in the slider under which the strap was passed; wherein an attachment pin, sized to be inserted into the attachment hole of the paddle, projects orthogonally from a top surface of the slider; wherein the attachment pin is shaped in such a way that the attachment pin has a throat section of a narrower width so that the throat section can be inserted into the key of the lock piece;

placing the crossbar assembly in the standard indentations of a treatment couch;

placing a body cushion over the crossbar assembly;

positioning a patient on the body cushion;

securing a paddle to each of the two sliders by placing the attachment hole of the paddle over the attachment pin of the respective slider and sliding the lock piece of the paddle towards the attachment pin such that the key engages the throat section of the attachment pin;

moving the coupled paddles and sliders into the desired position manually or by pulling downward on the straps;

securing the paddles and sliders in place by engaging the respective buckle lever; and allowing the body cushion to harden.

\* \* \* \* \*